(12) United States Patent
Koerner et al.

(10) Patent No.: US 9,597,113 B2
(45) Date of Patent: Mar. 21, 2017

(54) ENDOSCOPE AND SHAFT SYSTEM (75) Inventors: Eberhard Koerner, Knittlingen (DE); Mark Freier, Oberderdingen (DE)

(73) Assignee: Richard Wolf GmbH, Knittlingen (DE)

( * ) Notice: Subject to any disclaimer, the term of this patent is extended or adjusted under 35 U.S.C. 154(b) by 920 days.

(21) Appl. No.: 12/488,003

(22) Filed: Jun. 19, 2009

(65) Prior Publication Data
US 2009/0318763 A1 Dec. 24, 2009

(30) Foreign Application Priority Data
Jun. 19, 2008 (DE) .................. 10 2008 029 301

(51) Int. Cl.
| A61B 1/04 | (2006.01) |
| A61B 1/00 | (2006.01) |
| A61B 17/34 | (2006.01) |
| A61B 17/00 | (2006.01) |

(52) U.S. Cl.
CPC ...... *A61B 17/3421* (2013.01); *A61B 1/00128* (2013.01); *A61B 90/50* (2016.02); *A61B 2017/00261* (2013.01); *A61B 2017/3409* (2013.01); *A61B 2017/3445* (2013.01)

(58) Field of Classification Search
None
See application file for complete search history.

(56) References Cited

U.S. PATENT DOCUMENTS

| 5,707,340 | A | 1/1998 | Hipp et al. | |
| 6,142,931 | A * | 11/2000 | Kaji | 600/114 |
| 6,152,871 | A | 11/2000 | Foley et al. | |
| 6,196,967 | B1 * | 3/2001 | Lim et al. | 600/125 |
| 6,458,077 | B1 * | 10/2002 | Boebel et al. | 600/154 |
| 6,824,544 | B2 * | 11/2004 | Boebel et al. | 606/46 |
| 2003/0181906 | A1 * | 9/2003 | Boebel et al. | 606/46 |
| 2006/0063975 | A1 * | 3/2006 | Hipp et al. | 600/156 |
| 2007/0112254 | A1 * | 5/2007 | Weigel et al. | 600/137 |
| 2008/0208001 | A1 * | 8/2008 | Hadani | 600/128 |
| 2009/0030283 | A1 | 1/2009 | Freystein et al. | |
| 2009/0054728 | A1 * | 2/2009 | Trusty | A61B 1/00135 600/114 |

FOREIGN PATENT DOCUMENTS

| DE | 33 19 049 A1 | 5/1984 |
| DE | 44 44 049 A1 | 6/1996 |

(Continued)

OTHER PUBLICATIONS

Full translation of JP 02-297331.*
EP Search Report issued on Oct. 21, 2009 in EP Application No. 09 00 7594.

*Primary Examiner* — Anhtuan T Nguyen
*Assistant Examiner* — Alexandra Newton
(74) *Attorney, Agent, or Firm* — Panitch Schwarze Belisario & Nadel LLP (57) ABSTRACT An endoscope and shaft system include an access shaft and an endoscope which can be inserted into the access shaft, the proximal end of the access shaft has a grip part, and the endoscope is held in a connecting piece. The connecting piece can be detachably connected to the grip part, and the connecting piece can be rotated about the longitudinal axis of the endoscope relative to the grip part when the connecting piece is connected to the grip part.

22 Claims, 11 Drawing Sheets (56) References Cited

FOREIGN PATENT DOCUMENTS

| DE | 199 35 725 A1 | 2/2001 |
| DE | 202004014828 U1 | 12/2004 |
| DE | 10 2007 032 201 A1 | 1/2009 |
| EP | 0 455 188 A2 | 11/1991 |
| EP | 0 682 910 A1 | 11/1995 |
| JP | 58081029 A | 5/1983 |
| JP | S58-81029 A | 5/1983 |
| JP | 02297331 A | 12/1990 |
| JP | H02-297331 A | 12/1990 |

* cited by examiner

ENDOSCOPE AND SHAFT SYSTEM

BACKGROUND OF THE INVENTION

The invention relates to an endoscope and shaft system for use in endoscopic spinal surgery, particularly in the region of the cervical spine.

Due to anatomical considerations, endoscopic spinal surgery, particularly in the region of the cervical spine, can only utilize a small access channel, and accordingly it is only possible to use small-caliber endoscope and shaft systems. Optimal placement of the access shafts is difficult from the outset, and a subsequent correction is generally only possible using relatively high manipulation forces.

BRIEF SUMMARY OF THE INVENTION

In view of this problem, it is the object of the invention to provide an endoscope and shaft system which affords the possibility of transferring large manipulation forces onto the access shaft without damaging and negatively influencing the movability of the endoscope.

The endoscope and shaft system according to the invention has an access shaft and an endoscope which can be inserted into the access shaft. According to an embodiment of the invention, the proximal end of the access shaft has a grip part. The advantage of this is that manipulation forces can be directly transferred to the access shaft, via the grip part, in order to position the access shaft in the surgical site. In the process, the inserted endoscope remains free from the manipulation forces and is protected against damage. This affords the possibility of transferring comparatively large manipulation forces without having to design a particularly reinforced endoscope for this purpose. Hence, the endoscope can furthermore have a very slim design and be matched to the very small access channel available so that the available space can be utilized in an optimum manner.

The endoscope is held by a connecting piece. To this end, the endoscope is connected to the connecting piece in a preferably detachable manner. In turn, the connecting piece is or can be connected to the grip part in a preferably detachable manner. This affords the possibility of detaching the connecting piece, together with the endoscope, from the grip part and the access shaft so that, for example, other instruments can be guided to the surgical site through the access shaft. In this case, the access shaft can be handled solely by the grip part directly connected to the access shaft. Furthermore, the connecting piece can be rotated about the longitudinal axis of the endoscope relative to the grip part when the connecting piece is connected to the grip part. This affords the possibility of rotating the endoscope about its longitudinal axis in the access shaft so that a region of the surgical site which is as large as possible can be observed using the endoscope.

Preferably, the endoscope can not only be rotated but also be moved in the axial direction. Such axial movability can be achieved, for example, by the connecting piece not only being rotatable relative to the grip part but also being axially movable relative to the grip part. Then the endoscope is displaced axially and/or rotated together with the connecting piece such that the distal end of the endoscope is placed such that a desired region of the surgical site can be observed.

Hence, according to the invention, an endoscope and shaft system is provided which, firstly, affords the possibility of transferring relatively large manipulation forces and, secondly, simultaneously affords the possibility of moving the endoscope, preferably freely, in the access shaft.

Preferably, the grip part and/or the connecting piece are designed such that the endoscope, held in the connecting piece, is arranged with its longitudinal axis having a parallel offset to the longitudinal axis of the access shaft. This provides, in the cross section of the access shaft, a free lumen next to the endoscope through which a work instrument can be supplied, next to the endoscope, through the access shaft and to the surgical site.

More preferably, the access shaft has a cross-sectional shape which has a greater width in a first direction than in a second direction which is perpendicular to the first direction. This means that the access shaft does not have a circular cross section but rather a basically oval design. This affords the possibility of designing the cross section of the access shaft as having a height which is as small as possible so that the access shaft can easily be supplied to the region of the spine, in particular to the intervertebral space. At the same time, the larger cross-sectional width provides a sufficiently large lumen in the interior of the access shaft through which an endoscope and possibly further instruments can be supplied. As described above, the endoscope is preferably placed such that its longitudinal or central axis has a parallel offset to the longitudinal or central axis of the access shaft. This means that ideally the endoscope is located in one half of the oval cross section of the access shaft and the other half forms a free lumen through which, for example, a work instrument can be supplied.

In accordance with a further preferred embodiment, the access shaft is detachably connected to the grip part. As a result, the instrument can be combined with other instruments during the insertion into the intervertebral space and can be taken apart for cleaning or maintenance purposes or, for example, different access shafts can be connected to one and the same grip part. More preferably, the connection between the grip part and the access shaft is designed such that the access shaft can be connected to the grip part in two possible angular positions. This means that the access shaft can be connected to the grip part in a second possible position when rotated by 180 degrees about its own longitudinal axis. In the case of an oval design of the access shaft and an offset arrangement of the endoscope, the endoscope can be alternatively positioned in both possible positions in the access shaft. By way of example, the connection between the grip part and access shaft is designed as a detachable ball latch connection.

More preferably, the distal end of the grip part has a receptacle for the proximal end of the access shaft and the proximal end of the grip part has a receptacle for the connecting piece, these two receptacles being arranged having a parallel offset with respect to one another in a direction which is transverse to the longitudinal axis of the access shaft. This is how the grip part ensures the offset arrangement of endoscope and access shaft. When the endoscope is connected to the connecting piece, the connecting piece is positioned, in a defined manner by means of the grip part, in the direction across the longitudinal axis of the access shaft. However, at the same time, the ability of the endoscope to rotate about its longitudinal axis and, preferably, also the axial movability of the endoscope in the access shaft remain ensured.

Preferably, the grip part and the connecting piece are detachably plugged together in the axial direction. This makes an easy removal of the connecting piece from the grip part possible in order, for example, to take the endoscope connected to the connecting piece out of the access shaft. This can be necessary if the entire cross section of the access shaft is required for removing relatively large amounts of tissue from the surgical site. As a result of the endoscope remaining connected to the connecting piece, removing the endoscope does not necessarily lead to the loss of the positioning of the endoscope. This means that when the connecting piece and grip part are again plugged together, the endoscope is again in the same positioning it was in before its removal. This is ensured by the fact that the connecting piece positions the endoscope, that is to say the connecting piece has a positioning means for positioning the endoscope in the access shaft. This can comprise positioning in the axial direction and/or positioning with respect to the angular position of the endoscope about its longitudinal axis.

The proximal end of the grip part preferably has a sleeve which engages into the interior of the connecting piece from the distal end. That is to say that the distal end of the connecting piece has an opening which is matched in size and cross-sectional shape to the shape and size of the external circumference of the sleeve on the grip part. The sleeve is preferably of circular-cylindrical design and the opening on the connecting piece has a corresponding cylindrical design. This affords the possibility of providing a relative large bearing face between the connecting piece and the grip part in order to ensure reliable positioning and guiding of the connecting piece on the grip part. The ability of the endoscope to rotate about its longitudinal axis is preferably obtained by the sleeve of the grip part being able to rotate in the interior of the opening on the distal side of the connecting piece. That is to say that the connecting piece rotates, preferably freely, on the sleeve on the grip part.

Furthermore, it is preferable for the proximal end of the connecting piece to have an attachment receptacle for detachably attaching the endoscope. As a result of this attachment receptacle, the endoscope is held or positioned on the connecting piece in a defined manner. In the process, it is preferable for the endoscope to be able to be detached from the connecting piece for cleaning and maintenance purposes. Furthermore, this affords the possibility of attaching different endoscopes on one and the same connecting piece.

The detachable attachment of the endoscope is preferably made possible as a result of the endoscope being detachably fixed to at least one bearing face of the attachment receptacle by means of a rotatable clamping ring which has an internal diameter which varies over the circumference. The clamping ring is designed such that, in a detached position, it is positioned such that there is a relatively large distance between the clamping ring and bearing face and so the endoscope can be moved between the two. Rotating the clamping ring causes a region with a smaller internal diameter to cover the bearing face. As a result of this, the radial distance between the clamping ring and the bearing face decreases and so an appropriate attachment section of the endoscope can be clamped in between the clamping ring and the bearing face. Here, the attachment receptacle is furthermore preferably designed such that there is interlocking positioning of the endoscope in addition to this force-fit clamping so as to hold the endoscope in a defined position.

The attachment receptacle is preferably formed by a sleeve which has a sector-shaped cutout at its proximal end, with the end faces of the sleeve facing the cutout forming bearing faces for the endoscope. The endoscope has a corresponding attachment section which can be inserted into this sector-shaped cutout. In the process, bearing faces formed on the endoscope butt against the bearing faces of the recess, that is to say the end faces on the cutout of the sleeve. If provision is made for a clamping ring as described above, it is preferable for the bearing faces of the endoscope to be pressed against these end faces of the sleeve by rotation of the clamping ring and thus be fixed on the sleeve.

In accordance with a further preferred embodiment, the connecting piece has an adjustment device by means of which the endoscope can be moved axially relative to the grip part. That is to say that axial positioning of the endoscope in the access shaft is possible by means of the connecting piece. The advantage of arranging the adjustment device on the connecting piece is that when the connecting piece is separated from the grip part, the settings of the adjustment device are independent thereof or are not influenced thereby, so that when the connecting piece is again connected to the grip part, the previous positioning of the endoscope in the access shaft is restored.

In order to form the adjustment device, the connecting piece more preferably has two interlocking sleeves which engage into one another by means of a thread, an adjustment ring being arranged on a first sleeve for the purpose of being rotated and thus axially adjusting the first sleeve relative to the second sleeve. Preferably, the endoscope is attached to one of these sleeves in the manner described above. The adjustment ring is preferably applied to the other sleeve. Preferably, a sealing ring is provided on the sleeve without an adjustment ring in order to thus fix the endoscope. More preferably, the sleeve with the adjustment ring is plugged onto a sleeve formed on the proximal end of the grip part, as described above. This affords the possibility of the sleeve also being plugged, as described above. This affords the possibility of the sleeve with the adjustment ring being rotated on the sleeve of the grip part in order to rotate the endoscope about its longitudinal axis. More preferably, the sleeve on the grip part extends far into the interior of the connecting piece that it also engages into the second sleeve which engages with the sleeve with the adjustment ring via the thread. More preferably, the outer one of the two thread sleeves has a radially inwardly extending collar on the axial end facing away from the thread, which collar has an internal diameter which is basically the same as the internal diameter of the inner one of the two thread sleeves. This ensures that the two thread sleeves abut on the external circumference of the sleeve of the grip part. This ensures an improved guiding and positioning of the connecting piece on the grip part.

Furthermore, it is preferable for a spring element to be arranged between the two sleeves, engaging via the threads, and for the spring element to effect a clamping force between the two sleeves. Such a spring element can thus remove the play in the thread or keep it constant so that the two sleeves can preferably be adjusted with respect to one another without play and with a certain stiffness. This makes a very precise adjustment possible and avoids an inadvertent adjustment. The spring element can be designed as a spring tongue which extends in the circumferential direction and is formed by a partition in the sleeve wall, which extends in a substantially U-shaped manner. In this manner, the spring element can be formed, for example, in the outer one of the two sleeves and can be pressed radially inward against the inner one of the thread sleeves by a surrounding, annular clamping element.

Furthermore, it is preferable for the grip part and the connecting piece to have a free lumen extending axially in their interiors, the free lumen being flush with the free lumen in the interior of the access shaft. This means that if the endoscope is inserted into the access shaft, a free lumen remains therein, next to the endoscope, the proximal side of the lumen being flush with the free lumen in the grip part and the connecting piece so that a continuously free channel extends from the proximal to the distal end of the instrument. Instruments can be inserted through this free channel. In order to provide this continuously free lumen, the endoscope is preferably arranged eccentrically on the internal circumference of the connecting piece and the grip part so that the free lumen remains next to it.

More preferably, in the region of the connecting piece, the cross section of the endoscope has a roof-edge-shaped design so that it basically only fills one sector, which is less than 180 degrees, of an inner cross section of the connecting piece. This refinement affords the possibility of the continuous free lumen remaining intact over an angle of rotation which is as large as possible, even when the endoscope is rotated together with the connecting piece. Hence, a free sector which is larger than 180 degrees remains in the connecting piece when the endoscope is inserted, so that an approximately arc-shaped free space remains. When rotating the connecting piece, this free sector or arc sweeps over the proximal end of the free lumen of the access shaft so that a continuous through-passage through the connecting piece remains, even during rotation.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

The endoscope and shaft system according to the invention shown as an exemplary embodiment basically consists of two components: the first component is formed by an access shaft 2 and a grip part 4 which is detachably connected to the access shaft 2. To this end, the distal end of the grip part 4 is designed in a known manner with a receptacle for the proximal end of the access shaft 2 by means of a latching connection.

The second component is formed by a connecting piece 6 and an endoscope 8. The endoscope 8 is inserted into the connecting piece 6 from the proximal end, so that the optical shaft 10 of the endoscope extends into the access shaft 2 in the distal direction. The endoscope 8 is detachably connected to the connecting piece 6, as will be described in more detail below.

At its proximal end, the access shaft 2 terminates at a connector piece 12. The latter is inserted in a receptacle 14 on the distal side of the grip part 4 and is connected there to the grip part 4 in a detachable and interlocking manner by means of the latching elements 16.

The grip 18 which extends radially outward is an essential component of the grip part 4. The grip is directly connected to the access shaft 2, via the receptacle 14 and the connector piece 12, so that manipulation forces can be transferred directly onto the access shaft 2, via the grip 18, without the endoscope 8 being loaded by these forces. This affords the possibility of applying relatively high manipulation forces onto the access shaft 2.

Figure 8:
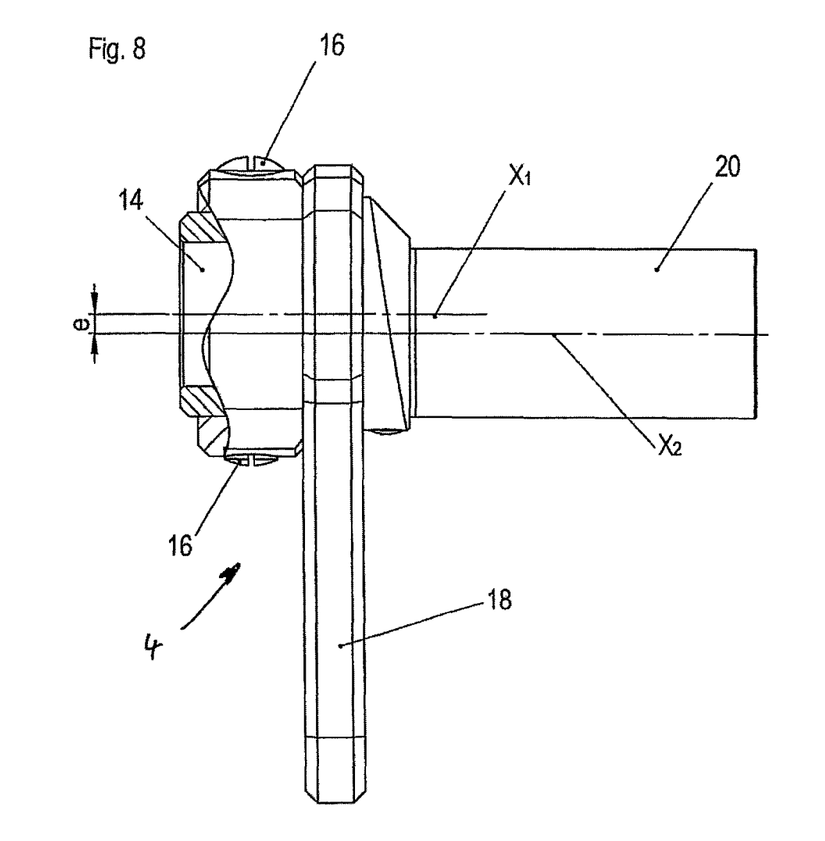
FIG. 8 is a detailed view of the grip part.

As can be seen best in the detailed view of FIG. 8, the grip part 4 has a cylindrical sleeve 20 at its proximal end. The sleeve is used for the connection to the connecting piece 6 and, for this purpose, is inserted into the connecting piece 6 from the distal end. The grip part 4 and the connecting piece 6 are thus easily plugged together and can easily be separated from one another. FIG. 8 shows that the longitudinal axis $X_1$ of the cylindrical receptacle 14 and the longitudinal axis $X_2$ of the sleeve 20 are arranged having a parallel offset with respect to one another by an amount e, that is to say they are offset in the lateral direction.

Figure 1:
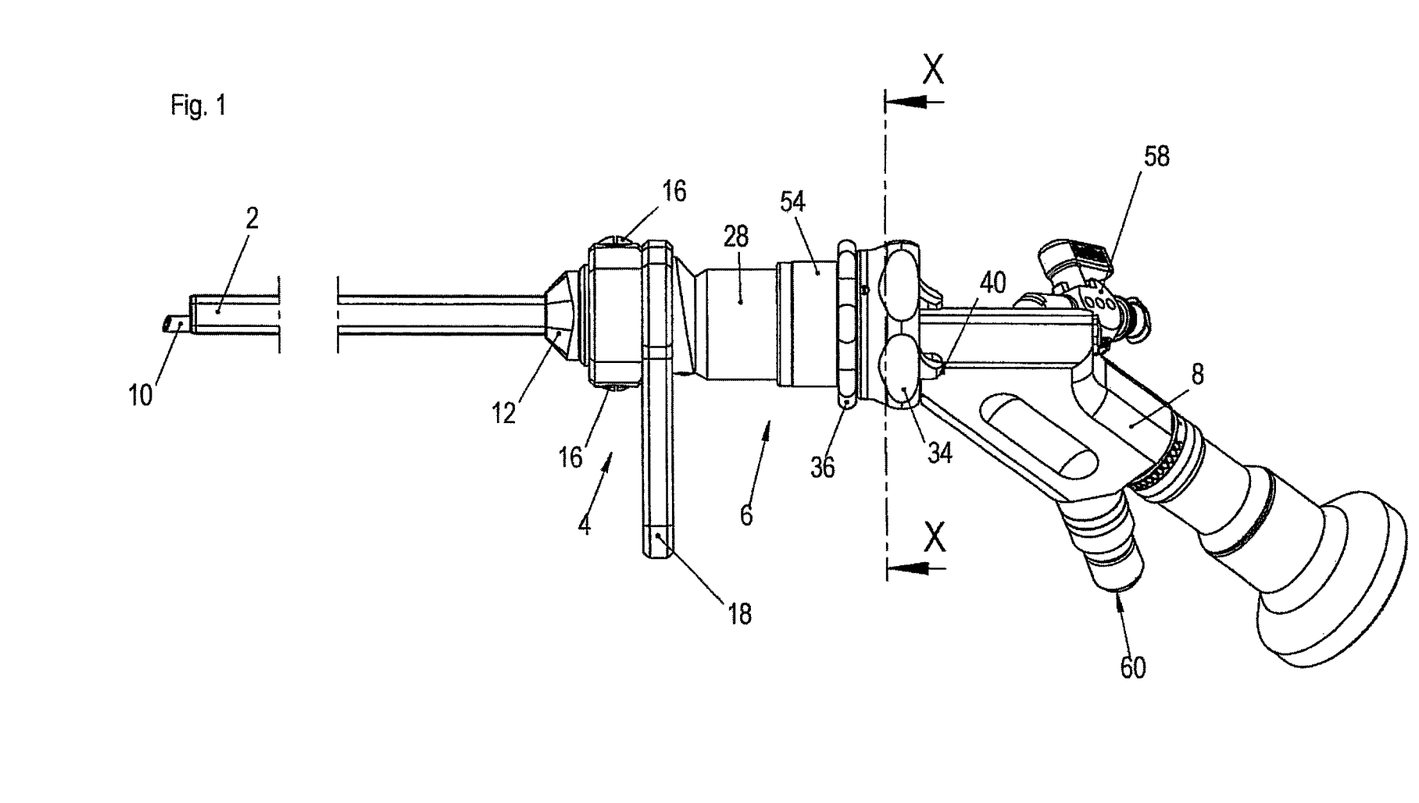
FIG. 1 is a schematic overview of an endoscope and shaft system according to an embodiment of the invention in the assembled state.
Figure 2:
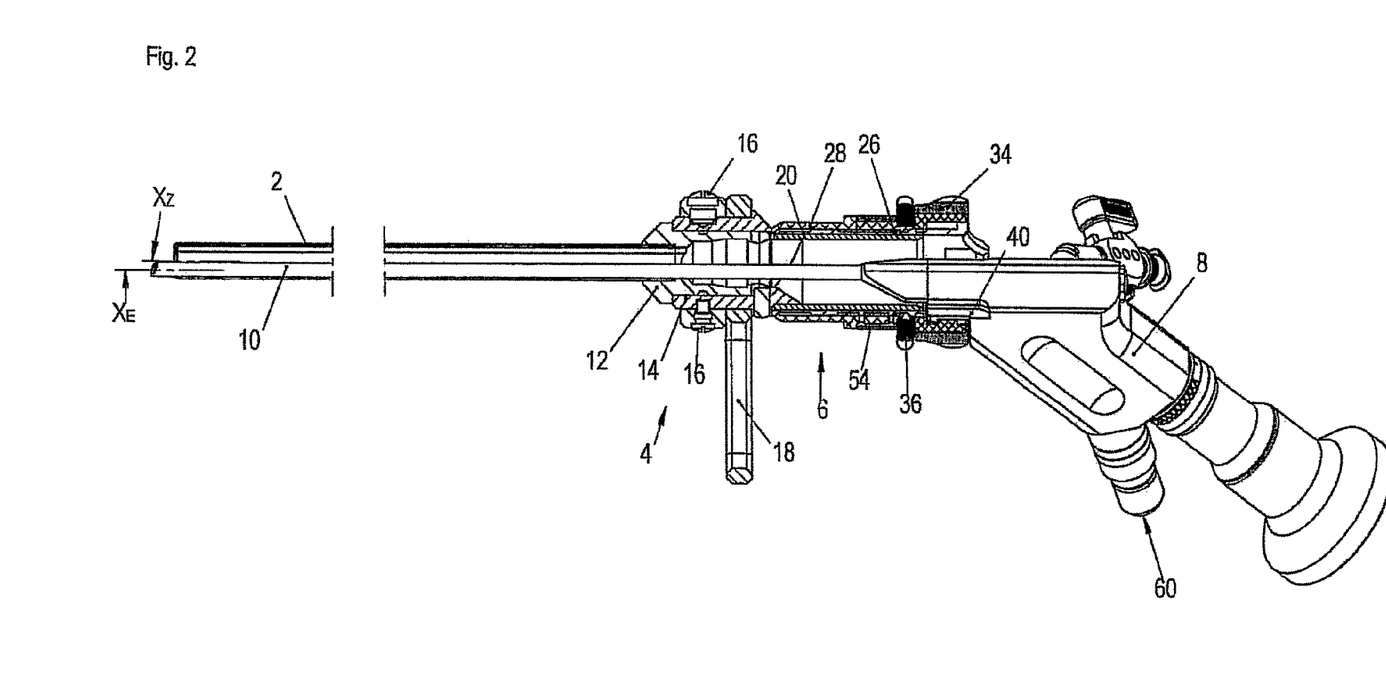
FIG. 2 is a partly cut away view of the endoscope and shaft system in accordance with FIG. 1.
Figure 3:
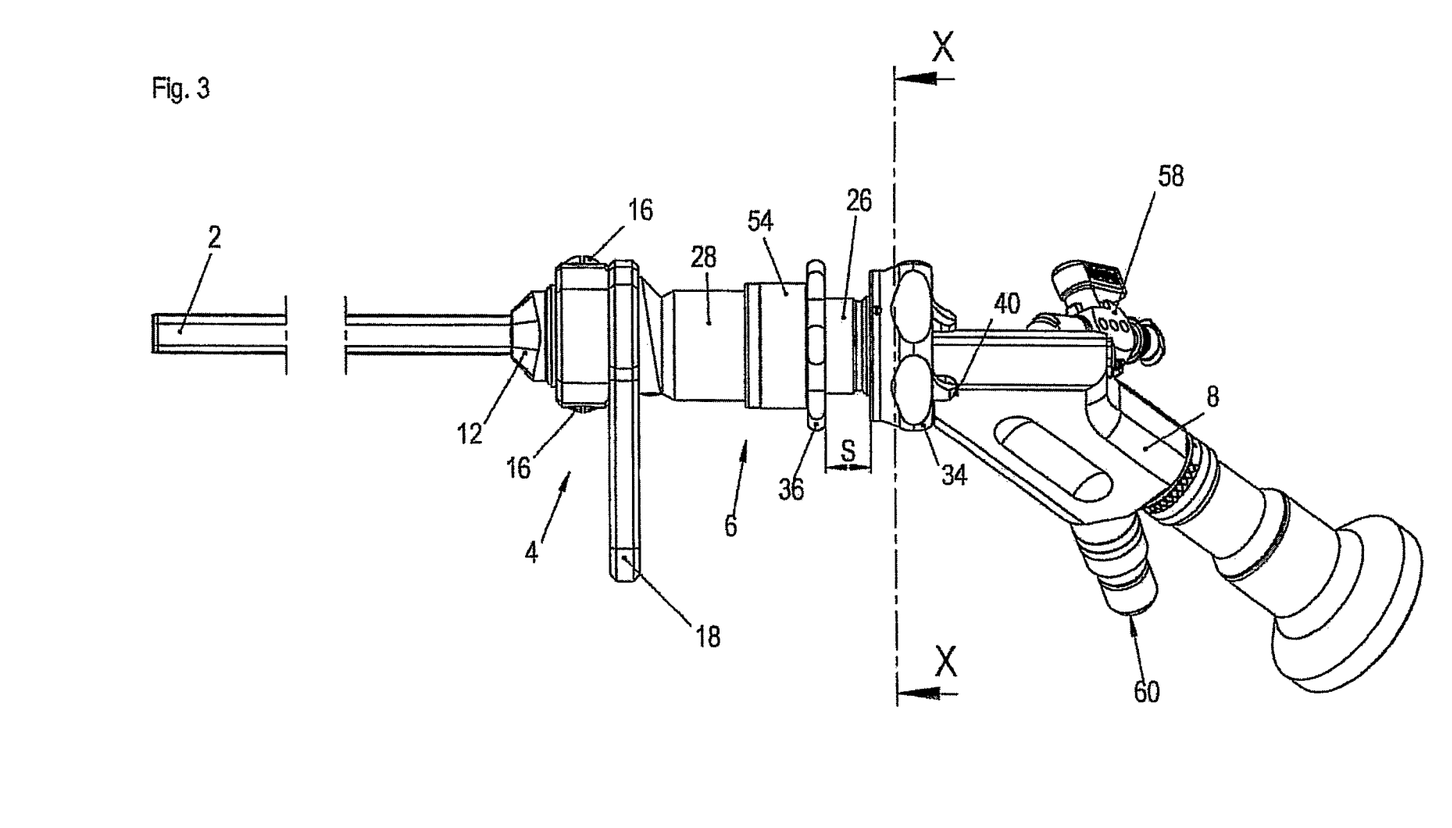
FIG. 3 is an endoscope and shaft system in accordance with FIG. 1 with a proximally displaced endoscope.
Figure 4:
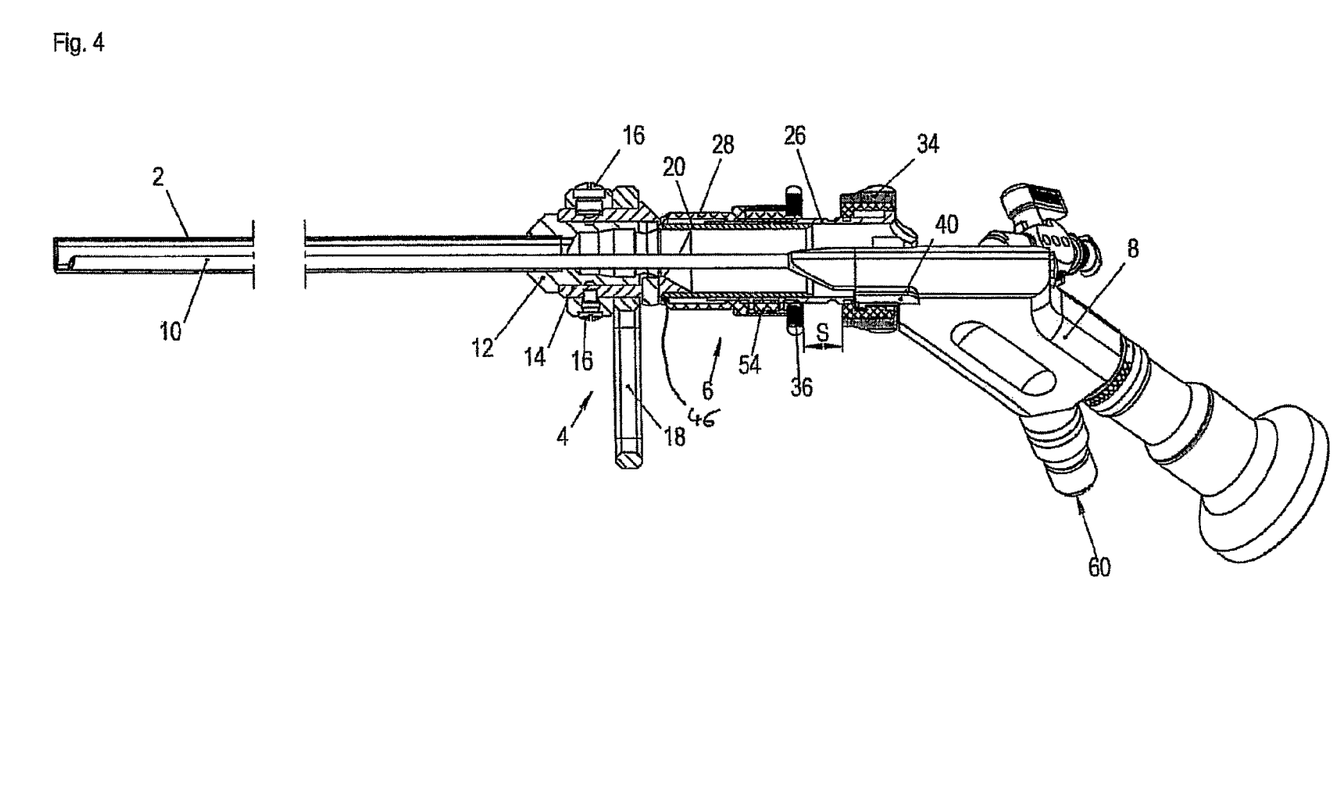
FIG. 4 is a sectional view of the endoscope and shaft system shown in FIG. 3.
Figure 5:
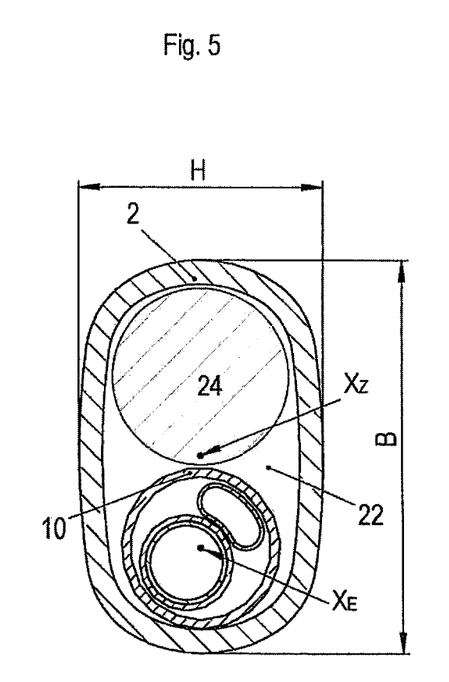
FIG. 5 is a cross-sectional view of the access shaft with an endoscope lying therein.
Figure 7:
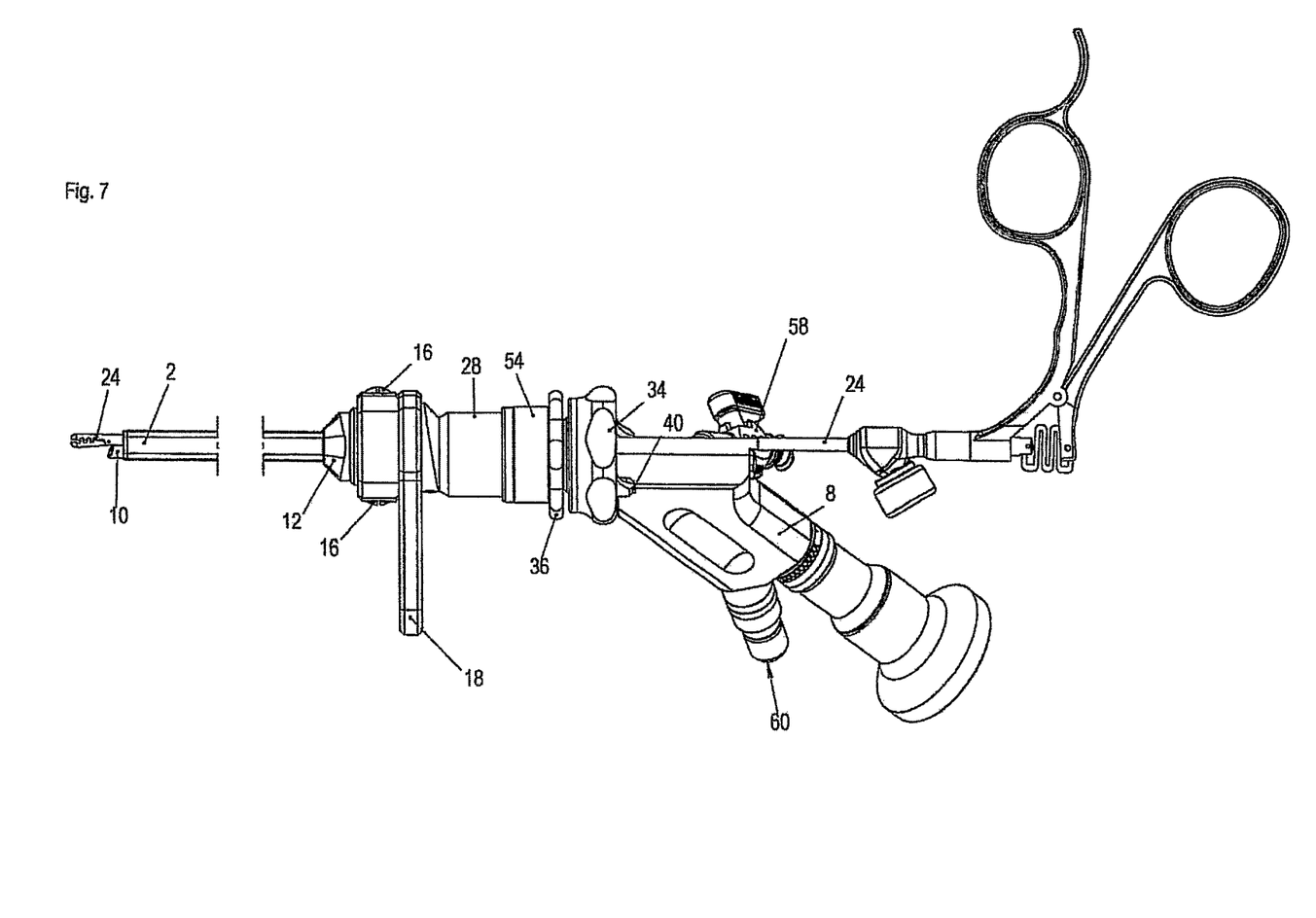
FIG. 7 is an overview of the instrument in accordance with FIGS. 1 to 6 with an inserted auxiliary instrument.

The offset e of the sleeve 20 with respect to the receptacle 14 in the grip part 4 is connected to the embodiment of the access shaft 2. FIG. 5 shows a cross section of the access shaft. It can be seen that the access shaft 2 basically has an oval cross section. That is to say that the extent or width B of the access shaft in a first cross-sectional direction is greater than the extent or height H in a second cross-sectional direction which is perpendicular to the first cross-sectional direction. The optical shaft 10 is not arranged centrally in the interior of the access shaft 2, but rather it is arranged, laterally offset, in one half of the inner cross section of the access shaft 2. This means that the longitudinal axis $X_E$ of the optical shaft 10 has a parallel offset to the longitudinal or central axis $X_Z$ of the access shaft 2 which extends as a continuation of the longitudinal axis $X_1$ of the receptacle 14. Thus a free lumen 22 remains, into which a work instrument 24 can be inserted. By way of example, this can be forceps, as illustrated in FIG. 7. Hence, the endoscope or optical shaft 10 and the work insert 24 fill the inner cross section of the access shaft 2 in an optimum manner, with the height H of the access shaft 2 at the same time being kept low so that the instrument can also be moved to the surgical site via narrow access channels. The optical shaft 10 is arranged in the interior of the access shaft 2, offset to one side in one half with respect to the central axis $X_Z$ of the access shaft 2, as a result of the offset e between the sleeve 20 and receptacle 14 in the grip part 4. At the same time, the offset e ensures that the endoscope 8 remains rotatable about the longitudinal axis of the endoscope or optical shaft 10, in order to be able to rotate the field of view in the surgical site. This rotation is achieved by the connecting piece 6 on the sleeve 20 of the grip part 4 being able to be rotated about the longitudinal axis $X_2$ of the sleeve 20. In the process, the endoscope 8 is positioned in the connecting piece 6 such that the longitudinal axis $X_E$ of the optical shaft 10 extends along the longitudinal axis $X_2$ of the connecting piece 6 and of the sleeve 20.

Figure 9:
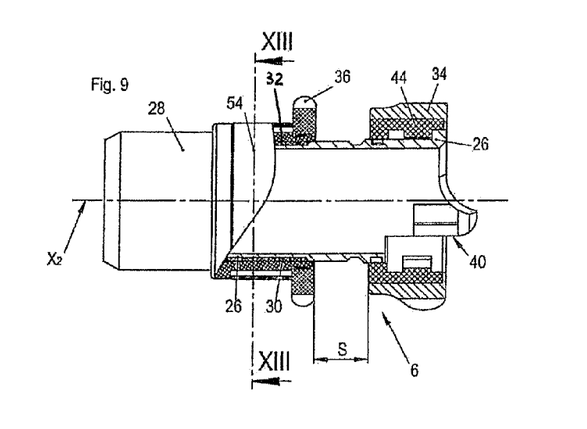
FIG. 9 is a sectional view of the connecting piece.

The connecting piece 6 basically consists of an inner sleeve 26 and an outer sleeve 28 which engage into each other via threads 30 and 32; this can best be seen in the detailed view of FIG. 9. The thread 30 is designed as a male thread on the inner sleeve 26, and the thread 32 is designed as a female thread on the inner side of the outer sleeve 28. In the proximal direction, the inner sleeve 26 extends beyond the outer sleeve 28. There the sleeve is provided with a sealing ring 34 on the external circumference. On the external circumference, the outer sleeve 28 is provided with an adjustment ring 36 which protrudes radially outward. The inner sleeve 26 and outer sleeve 28 can be grasped by the sealing ring 34 and the adjustment ring 36 and rotated against one another. As a result of the thread engagement, they move apart or together in the axial direction, depending on the direction of rotation. This makes an axial feed by the amount s possible. The endoscope 8 is fixed at the proximal end of the inner sleeve 26, as will be explained in more detail below. As a result of this, when the outer sleeve 28 is adjusted with respect to the inner sleeve 26, the endoscope is also moved relative to the grip part 4 connected to the connecting piece 6 via the outer sleeve 28 and hence the endoscope is moved in the axial direction in the access shaft 2. This affords the possibility of the distal end of the endoscope likewise being moved by the amount s by rotating the two sleeves of the connecting piece 6.

In order to connect the inner sleeve 26 to the endoscope 8, the proximal end of the former has a sector-shaped cutout 38 which opens toward the proximal end. Two bearing faces 40 form the end faces of the sleeve 26, which extend in the longitudinal direction of the sleeve 26 and delimit the recess 38. The endoscope 8 has two shoulders 41 which project toward opposite sides and extend parallel to the longitudinal direction $X_E$ of the endoscope. These shoulders 41 form bearing faces 42 which lie opposite the bearing faces 40 on the sleeve 26 and abut against the latter. The width of the endoscope 4 between the shoulders 41 is selected such that it corresponds to the width of the recess 38. This affords the possibility of inserting the endoscope 8 into the cutout 38 in the sleeve in an interlocking manner. In the process, the endoscope 8 is situated such that the endoscope shaft 10 extends centrally in the sleeve 26 in the direction of the longitudinal axis $X_2$ of the latter. The endoscope is fixed by a clamping ring 44 which surrounds the inner sleeve 26 at the external circumference and is situated in the interior of the annular sealing ring 34. The clamping ring 44 can be rotated with the sealing ring 34 about the sleeve 26 in the direction of arrows A and Z. Rotation in the A direction effects a rotation into the opened position, shown in FIG. 10. Rotation in the Z direction effects a rotation into the closed position, shown in FIG. 11. In the closed position, the endoscope 8 is pressed against the bearing faces 40 and hence clamped. This is effected by the clamping ring 44 having a diameter or radius on the internal circumference which varies over the circumference. In the detached position in FIG. 10, a region of the clamping ring with a larger radius $r_1$ lies above the endoscope 8. Thus, a certain amount of play remains between the clamping ring and the endoscope 8 so that the latter is not clamped. In the case of rotation in the direction of the arrow Z, the region of the clamping ring 44 with a smaller inner radius $r_2$ comes to rest over the endoscope 8, as shown in FIG. 11, so that the bearing faces 42 of the endoscope 8 are pressed without play against the bearing faces 40 on the inner sleeve 26, and hence the endoscope is fixed on the sleeve 26 and thus in the connecting piece 6.

When the endoscope 8 is fixed in the connecting piece 6, it can be taken from the grip part 4 together with the connecting piece 6 and hence be removed from the access shaft 2. This can be necessary if the entire inner cross section of the access shaft is required in order, for example, to remove relatively large amounts of tissue from the surgical site. Since the sleeves 26 and 28 of the connecting piece 6 are not rotated with respect to one another while the endoscope 4 is removed from the access shaft 2, the positioning of the endoscope 4 in the axial direction is maintained. This means that when the endoscope 8 is again inserted into the access shaft 2 and the connecting piece 6 is connected to the grip part 4, the endoscope 8 is again located in the same axial position as before its removal.

The connecting piece 6 and the grip part 4 engage such that the sleeve 20 on the proximal side of the grip part 4 extends into the inner sleeve 26 of the connecting piece 6. The external diameter of the sleeve 20 corresponds to the internal diameter of the inner sleeve 26. Additionally, the outer sleeve 28 is provided at its distal end with a radially inwardly oriented annular collar 46 which likewise butts against the external circumference of the sleeve 20. This ensures safe bearing of the connecting piece 6 on the sleeve 20 even if the inner sleeve is adjusted in the proximal direction and the maximum distance s is obtained between the inner sleeve 26 and the outer sleeve 28.

Figure 13:
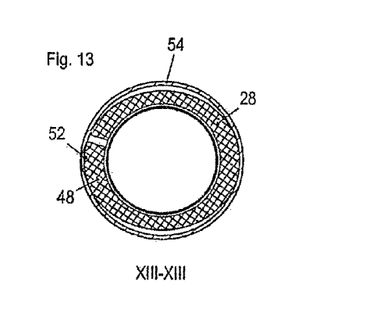
FIG. 13 is a sectional view along the line XIII-XIII in FIG. 12.

In order to ensure a play-free adjustment of the sleeves 26 and 28 with a certain amount of stiffness by the threads 30, 32 engaging, the outer sleeve 28 is provided with a spring element in the region where the thread engages with the inner sleeve 26. The spring element is designed as a tongue 48 extending in the circumferential direction. The tongue 48 is in this case formed by a partition 50 extending in a substantially U-shaped manner in the wall of the sleeve 28. This partition 50 extends through the entire width of the wall of the sleeve 28, from the external circumference to the internal circumference. The tongue 48 formed in this manner is provided at its free end with a radially outwardly projecting bead 52. FIG. 13 shows that the external circumference of the sleeve 28 is basically oval in the region in which the tongue 48 is formed. In this region, the sleeve is surrounded in a circumferential manner by a tensioning ring 54. In the process, the bead 52 butts against the interior circumference of the tensioning ring 54. The effect of this is that the tongue 48 is pressed inward against the external circumference of the inner sleeve 26. This leads to clamping between the inner sleeve 26 and the outer sleeve 28 which eliminates the play from the engagement of the threads 30 and 32.

Figure 6:
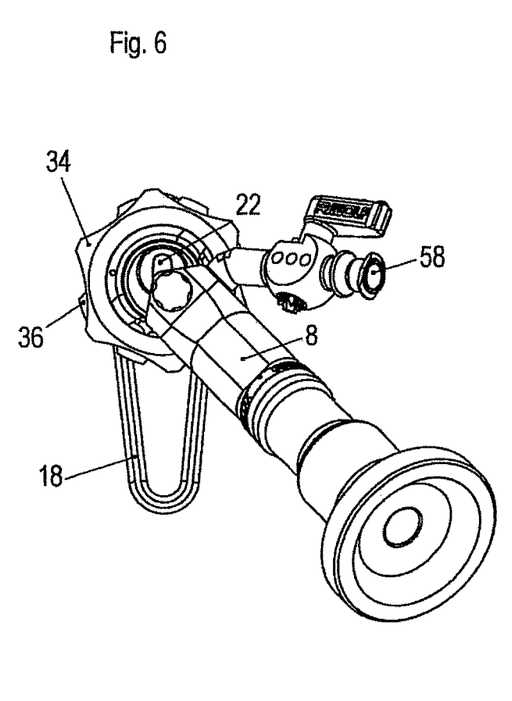
FIG. 6 is a plan view of the instrument in accordance with FIGS. 1 to 4, as seen from the proximal side.
Figure 10:
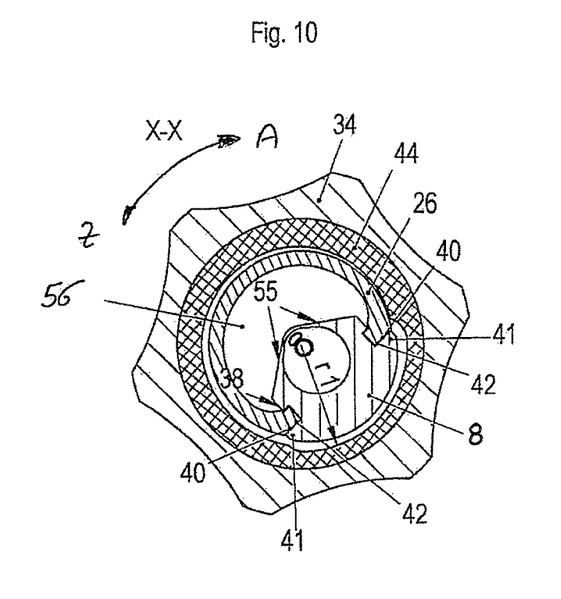
FIG. 10 is sectional view along the line X-X in FIG. 1.
Figure 11:
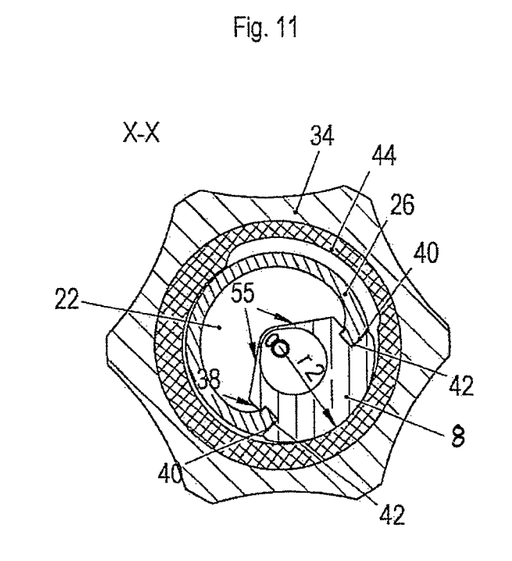
FIG. 11 is a view in accordance with FIG. 10, the endoscope being in the clamped state.
Figure 12:
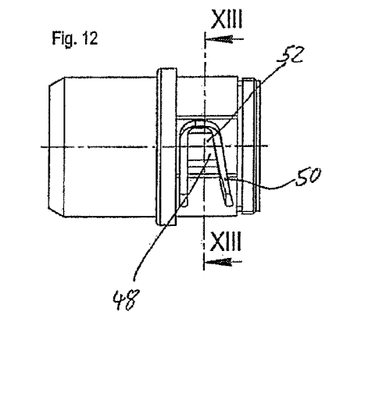
FIG. 12 is a detailed view of the outer sleeve of the connecting piece.

FIGS. 6, 10 and 11 show that the endoscope 8 is designed with a roof-edge-shaped cross section in the region in which it engages into the recess or cutout 38 of the sleeve 26, the oblique external sides 55 basically running tangential to the external circumference of the optical shaft 10. The advantage of this refinement of the endoscope in this region is that, in the cross section of the interior space of the sleeve 26, the endoscope only covers a sector of less than 180 degrees. Most of the cross section remains free and forms a free lumen 56. The free lumen covers the end face of the access shaft 2 in the region of the free lumen 22 of the latter which is provided to hold the work instrument 24. This affords the possibility of nonetheless rotating the endoscope 8 through a large angle region about its longitudinal axis $X_E$ by rotating the sleeve 26 on the sleeve 20, even if such a work instrument 24 is inserted into the access shaft 2. In the process, the free lumen 56 of the sleeve 26 sweeps over, in an arc shape, the region which is provided to hold the work instrument 24. Hence the free lumen 56 of the sleeve 26 and the free lumen 22 of the access shaft are flush and form a common free lumen from the proximal to the distal end. This affords the possibility of rotating the endoscope 8 until the work instrument 24 butts against one of the two oblique faces 55 of the roof-edge profile of the endoscope 4.

Hence, overall, provision is made for an endoscope and shaft system which firstly affords the possibility of transferring large manipulation forces onto the access shaft 2 and at the same time allows a large movability of the endoscope 8 in the interior of the access shaft 2. The endoscope 8 can be moved in the axial direction $X_E$ and can be rotated about its longitudinal axis $X_E$. At the same time, the endoscope 8 remains completely free from manipulation forces which can be transferred onto the access shaft from the grip 18. Moreover, the endoscope 8 has a conventional design, that is to say it has optics, optical waveguides for illumination, and a rinsing channel. A rinsing connector 58 and an optical wave guide connector 60 are provided on the proximal end for the latter.

In place of the optical system, provision can be made for a CCD element or the like, and instead of the optical waveguides, provision can be made for one or more LEDs, as is conventional, for example, in a video endoscope.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An endoscope and shaft system comprising an access shaft (2), an endoscope (8), a grip part (4), and a connecting piece (6),
the access shaft (2) having a central longitudinal axis and a proximal end,
the grip part (4) having a distal receptacle (14) for receiving the proximal end of the access shaft (2) and a proximal receptacle (20) for receiving the connecting piece (6), the distal and proximal receptacles having central longitudinal axes being arranged offset with respect to one another in a direction transverse to the central longitudinal axis of the access shaft,
the connecting piece (6) being detachably plugged together with the grip part (4) along a central longitudinal axis of the endoscope (8) by connection of a distal end of the connecting piece with the proximal receptacle, wherein the proximal receptacle has a sleeve (20) which engages into an interior of the distal end of the connecting piece (6), such that the connecting piece is rotatable and axially adjustable relative to the proximal receptacle of the grip part (4), and
the endoscope (8) comprising an optical shaft (10) insertable into the access shaft (2) and having a central longitudinal axis, the endoscope being held in the connecting piece (6) when the optical shaft is inserted in the access shaft (2), such that the endoscope is rotatable about its central longitudinal axis together with the connecting piece (6) in the proximal receptacle of the grip part (4), and such that the endoscope is axially displaceable relative to the grip part when the connecting piece is plugged together with the grip part.

2. The endoscope and shaft system as claimed in claim 1, wherein the grip part (4) and/or the connecting piece (6) is designed such that when the endoscope (8) is held in the connecting piece (6), the optical shaft (10) is rotatable about its central longitudinal axis and is arranged with its central longitudinal axis having a parallel offset to the central longitudinal axis of the access shaft (2).

3. The endoscope and shaft system as claimed in claim 1, wherein the access shaft (2) has a cross-sectional shape which has a greater width in a first direction than in a second direction which is perpendicular to the first direction.

4. The endoscope and shaft system according to claim 1, wherein the access shaft (2) is detachably connected to the grip part (4).

5. The endoscope and shaft system as claimed in claim 1, wherein a proximal end of the connecting piece (6) has an attachment receptacle (38) for detachably attaching the endoscope (8).

6. The endoscope and shaft system as claimed in claim 5, wherein the endoscope (8) is detachably fixed to at least one bearing face (40) of the attachment receptacle (38) by a rotatable clamping ring (44) which has an internal diameter which varies over its circumference.

7. The endoscope and shaft system as claimed in claim 6, wherein the attachment receptacle is formed by a sleeve (26) which has a sector-shaped cutout (38) at a proximal end thereof, with end faces of the sleeve (26) facing the cutout (38) forming bearing faces (40) for the endoscope (8).

8. The endoscope and shaft system as claimed in claim 1, wherein the grip part (4) and the connecting piece (6) have a free lumen (56) extending axially in their interiors, the free lumen (56) being flush with a free lumen (22) in an interior of the access shaft (2).

9. The endoscope and shaft system as claimed in claim 1, wherein, in a region of the connecting piece (6), the endoscope (8) essentially fills only one sector, which is less than 180 degrees, of an internal cross section of the connecting piece (6).

10. The endoscope and shaft system as claimed in claim 1, wherein the connecting piece is directly connected to the grip part when the grip part and the connecting piece are plugged together.

11. An endoscope and shaft system comprising an access shaft (2), an endoscope (8), a grip part (4), and a connecting piece (6),
the access shaft (2) having a central longitudinal axis and a proximal end,
the grip part (4) having a distal receptacle (14) for receiving the proximal end of the access shaft (2) and a proximal receptacle (20) for receiving the connecting piece (6), the distal and proximal receptacles having central longitudinal axes being arranged offset with respect to one another in a direction transverse to the central longitudinal axis of the access shaft,
the connecting piece (6) being detachably plugged together with the grip part (4) along a central longitudinal axis of the endoscope (8) by connection of a distal end of the connecting piece with the proximal receptacle, wherein the connecting piece (6) has an adjustment device by which the endoscope (8) is axially displaceable relative to the grip part (4), the adjustment device comprising two interlocking sleeves (26, 28) which engage into one another by a thread (30, 32) and an adjustment ring (36) arranged on a first sleeve (28) for being rotated and thus axially adjusting the first sleeve (28) relative to the second sleeve (26), such that the connecting piece is rotatable and axially adjustable relative to the proximal receptacle of the grip part (4), and the endoscope (8) comprising an optical shaft (10) insertable into the access shaft (2) and having a central longitudinal axis, the endoscope being held in the connecting piece (6) when the optical shaft is inserted in the access shaft (2), such that the endoscope is rotatable about its central longitudinal axis together with the connecting piece (6) in the proximal receptacle of the grip part (4), and such that the endoscope is axially displaceable relative to the grip part when the connecting piece is plugged together with the grip part.

12. The endoscope and shaft system as claimed in claim 11, wherein the proximal receptacle of the grip part (4) has a sleeve (20) which engages into an interior of the distal end of the connecting piece (6).

13. The endoscope and shaft system as claimed in claim 11, wherein a spring element (48) is arranged between the two interlocking sleeves (26, 28) and effects a clamping force between the two interlocking sleeves (26, 28).

14. The endoscope and shaft system as claimed in claim 11, wherein the grip part (4) and/or the connecting piece (6) is designed such that when the endoscope (8) is held in the connecting piece (6), the optical shaft (10) is rotatable about its central longitudinal axis and is arranged with its central longitudinal axis having a parallel offset to the central longitudinal axis of the access shaft (2).

15. The endoscope and shaft system as claimed in claim 11, wherein the access shaft (2) has a cross-sectional shape which has a greater width in a first direction than in a second direction which is perpendicular to the first direction.

16. The endoscope and shaft system according to claim 11, wherein the access shaft (2) is detachably connected to the grip part (4).

17. The endoscope and shaft system as claimed in claim 11, wherein a proximal end of the connecting piece (6) has an attachment receptacle (38) for detachably attaching the endoscope (8).

18. The endoscope and shaft system as claimed in claim 17, wherein the endoscope (8) is detachably fixed to at least one bearing face (40) of the attachment receptacle (38) by a rotatable clamping ring (44) which has an internal diameter which varies over its circumference.

19. The endoscope and shaft system as claimed in claim 18, wherein the attachment receptacle is formed by a sleeve (26) which has a sector-shaped cutout (38) at a proximal end thereof, with end faces of the sleeve (26) facing the cutout (38) forming bearing faces (40) for the endoscope (8).

20. The endoscope and shaft system as claimed in claim 11, wherein the grip part (4) and the connecting piece (6) have a free lumen (56) extending axially in their interiors, the free lumen (56) being flush with a free lumen (22) in an interior of the access shaft (2).

21. The endoscope and shaft system as claimed in claim 11, wherein, in a region of the connecting piece (6), the endoscope (8) essentially fills only one sector, which is less than 180 degrees, of an internal cross section of the connecting piece (6).

22. The endoscope and shaft system as claimed in claim 11, wherein the connecting piece is directly connected to the grip part when the grip part and the connecting piece are plugged together.

\* \* \* \* \*